United States Patent [19]

Iijima et al.

[11] Patent Number: 4,829,067

[45] Date of Patent: May 9, 1989

[54] BENZO-FURAN DERIVATIVE

[75] Inventors: Ikuo Iijima, Urawa; Masakatsu Ozeki, Wako; Yutaka Saiga, Ageo; Tohru Ishizuka, Kitamoto; Kunio Nosaka, Kasukabe, all of Japan

[73] Assignee: Tanabe Seiyaku Co., Ltd., Osaka, Japan

[21] Appl. No.: 127,406

[22] Filed: Dec. 2, 1987

[30] Foreign Application Priority Data

Dec. 2, 1986 [JP] Japan .................................. 61-287511

[51] Int. Cl.$^4$ .................. C07D 211/14; A61K 31/445
[52] U.S. Cl. .................. 514/233.5; 514/422; 514/320; 514/464; 514/465; 514/443; 514/324; 546/196; 546/202; 548/525; 544/153; 549/51; 549/49; 549/468; 549/469; 549/471
[58] Field of Search ......................... 549/468, 469, 471; 546/196; 548/525; 544/153; 514/320, 422, 233, 234, 464, 465

[56] References Cited

U.S. PATENT DOCUMENTS 3,452,033 6/1969 Mooradian .......................... 549/460
4,238,487 12/1980 Bicking ............................... 546/196

OTHER PUBLICATIONS

Lednicer et al., CA104:19499g.
Woyke et al., CA96:507c.
Zawadowski et al., CA100:120800r.

*Primary Examiner*—Jane T. Fan
*Attorney, Agent, or Firm*—Birch, Stewart, Kolasch & Birch

[57] ABSTRACT

Novel benzo-furan(or -thiophene) derivative of the formula:

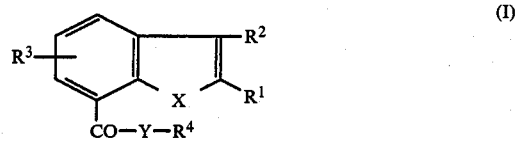

wherein $R^1$ is hydrogen atom, a lower alkyl group, a cycloalkyl group, a phenyl-lower alkyl group or a substituted or unsubstituted phenyl group, $R^2$ is hydrogen atom, a lower alkyl group, an acyl group or phenyl group, $R^3$ is hydrogen atom, a halogen atom, nitro group, a lower alkoxy group, amino group or an acylamino group, $R^4$ is a group of the formula:

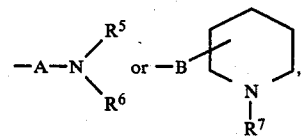

A is a lower alkylene group optionally substituted with hydroxy group, B is single bond or a lower alkylene group, one of $R^5$ and $R^6$ is hydrogen atom or a lower alkyl group and the other is a lower alkyl group or a phenyl-lower alkyl group, or $R^5$ and $R^6$ combine together with adjacent nitrogen atom to form a heteromonocyclic group, $R^7$ is a lower alkyl group, X is oxygen atom or sulfur atom, Y is oxygen atom, imino group, a lower alkylimino group or a phenyl-lower alkylimino group and a salt thereof are disclosed.

Said compound (I) and a salt thereof have a potent inhibitory activity against reflective contraction of urinary bladder.

9 Claims, No Drawings

BENZO-FURAN DERIVATIVE

This invention relates to a benzo-furan(or -thiophene) derivative and processes for preparing the same. More particularly, it relates to a benzo-furan(or -thiophene) derivative of the formula:

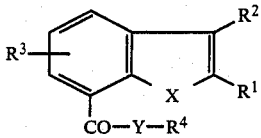

(I)

wherein $R^1$ is hydrogen atom, a lower alkyl group, a cycloalkyl group, a phenyl-lower alkyl group or a substituted or unsubstituted phenyl group, $R^2$ is hydrogen atom, a lower alkyl group, an acyl group or phenyl group, $R^3$ is hydrogen atom, a halogen atom, nitro group, a lower alkoxy group, amino group or an acylamino group, $R^4$ is a group of the formula:

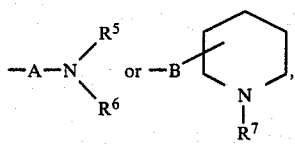

A is a lower alkylene group optionally substituted with hydroxy group, B is single bond or a lower alkylene group, one of $R^5$ and $R^6$ is hydrogen atom or a lower alkyl group and the other is a lower alkyl group or a phenyl-lower alkyl group, or $R^5$ and $R^6$ combine together with adjacent nitrogen atom to from a heteromonocyclic group, $R^7$ is a lower alkyl group, X is oxygen atom or sulfur atom, Y is oxygen atom, imino group, a lower alkylimino group or a phenyl-lower alkylimino group, or a salt thereof.

Pollakiuria (i.e., frequent micturition) is a symptom of diminution in effective bladder capacity and causes a person much trouble in his daily life. Since micturition is caused by reflective contraction of urinary bladder, a drug which inhibits the reflective contraction is useful for treatment of pollakiuria. A typical example of such a drug is flavoxate [chemical name: 2-piperidinoethyl 3-methyl-4-oxo-2-phenyl-4H-1-benzopyran-8-carboxylate (The Journal of Clinical Pharmacology, Vol. 10, 65–68 (1970))].

The compound (I) of the present invention and a salt thereof have potent inhibitory activity against the reflective contraction of the urinary bladder. For example, when 2-pyrrolidinoethyl 2-phenylbenzofuran-7-carboxylate was administered intravenously to anesthetized rats, the inhibitory activity of this compound against the reflective contraction of the urinary bladder was more than 1.5 times as strong as that of flavoxate.

Examples of the compound of the present invention include those of the formula (I) in which $R^1$ is hydrogen atom, a lower alkyl group (e.g., methyl, ethyl, propyl, butyl or pentyl), a cycloalkyl group (e.g., cyclopropyl, cyclopentyl or cyclohexyl), a phenyl-lower alkyl group (e.g., benzyl) or phenyl group, or $R^1$ is a phenyl group having a substituent selected from a halogen atom (e.g., chlorine, bromine or iodine), nitro group, a lower alkoxy group (e.g., methoxy, ethoxy, propoxy or butoxy), amino group, a di(lower alkyl)amino group (e.g., dimethylamino or diethylamino) and an acylamino group (e.g., a lower alkanoylamino group such as acetylamino or propionylamino, benzoylamino or benzylcarbonylamino); $R^2$ is hydrogen atom, a lower alkyl group (e.g., methyl, ethyl, propyl, butyl or pentyl), an acyl group (e.g., a lower alkanoyl group such as acetyl or benzoyl) or phenyl group; $R^3$ is hydrogen atom, a halogen atom (chlorine, bromine or iodine), nitro group, a lower alkoxy group (e.g., methoxy, ethoxy, propoxy, butoxy or pentyloxy), amino group or an acylamino group (e.g., a lower alkanoylamino group such as acetylamino or propionylamino, benzoylamino or benzylcarbonylamino); $R^4$ is a group of the formula:

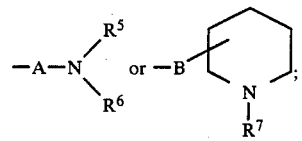

A is a lower alkylene group optionally substituted with hydroxy group (e.g., methylene, ethylene, trimethylene, tetramethylene, pentamethylene, 1-methylethylene, 1,1-dimethylethylene or 2-hydroxytrimethylene), B is single bond or a lower alkylene group (e.g., methylene, ethylene, trimethylene, tetramethylene or pentamethylene), one of $R^5$ and $R^6$ is hydrogen atom or a lower alkyl group (e.g., methyl, ethyl, propyl, butyl or pentyl) and the other is a lower alkyl group (e.g., methyl, ethyl, propyl, butyl or pentyl) or a phenyl-lower alkyl group (e.g., benzyl), or $R^5$ and $R^6$ combine together with adjacent nitrogen atom to form a heteromonocyclic group (e.g., pyrrolidino, piperidino or morpholino); $R^7$ is a lower alkyl group (e.g., methyl, ethyl, propyl, butyl or pentyl); X is oxygen atom or sulfur atom; Y is oxygen atom, imino group, a lower alkylimino group (e.g., methylimino, ethylimino, propylimino, butylimino or pentylimino) or a phenyl-lower alkylimino group (e.g., benzylimino or phenethylimino).

Among the compound (I) of the present invention, a preferred subgenus is those of the formula:

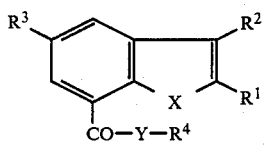

(i)

wherein $R^1$, $R^2$, $R^3$, $R^4$, X and Y are the same as defined above.

More preferred subgenus is those of the formula (i) in which $R^1$ is hydrogen atom, a $C_{1-4}$ alkyl group, a $C_{3-7}$cycloalkyl group, a phenyl-$C_{1-4}$alkyl group, phenyl group, a halogenophenyl group, nitrophenyl group, a $C_{1-4}$alkoxyphenyl group, aminophenyl group, a di($C_{1-4}$alkyl)amino-phenyl group or a $C_{2-5}$alkanoylaminophenyl group; $R^2$ is hydrogen atom, a $C_{1-4}$alkyl group, a $C_{2-5}$alkanoyl group, benzoyl group or phenyl group; $R^3$ is hydrogen atom, chlorine atom, nitro group, a $C_{1-4}$alkoxy group, amino group or a $C_{2-5}$alkanoylamino group; $R^4$ is a group of the formula:

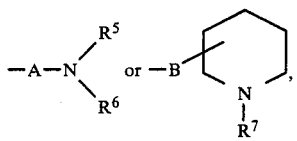

A is a $C_{1-6}$alkylene group optionally substituted with hydroxy group; B is single bond or a $C_{1-6}$alkylene group; one of $R^5$ and $R^6$ is hydrogen atom or a $C_{1-4}$alkyl group and the other is a $C_{1-4}$alkyl group or benzyl group, or $R^5$ and $R^6$ combine together with adjacent nitrogen atom to form pyrrolidino, piperidino or morpholino group; $R^7$ is a $C_{1-4}$alkyl group; X is oxygen atom or sulfur atom; Y is oxygen atom, imino group, a $C_{1-4}$alkylimino group or a phenyl-$C_{1-4}$alkylimino group.

Another preferred subgenus is those of the formula (i) in which $R^1$ is hydrogen atom, a $C_{1-4}$alkyl group or nitrophenyl group, $R^2$ is hydrogen atom or a $C_{2-4}$alkanoylamino group, $R^4$ is a group of the formula:

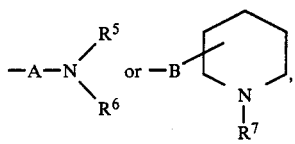

A is a $C_{1-4}$alkylene group, B is a $C_{1-4}$alkylene group, $R^5$ and $R^6$ combine together with adjacent nitrogen atom to form pyrrolidino, piperidino or morpholino group, and $R^7$ is a $C_{1-4}$alkyl group.

Further preferred subgenus is those of the formula (i) in which $R^1$ is hydrogen atom, methyl, phenyl or nitrophenyl group, $R^2$ is hydrogen atom or phenyl group, $R^3$ is hydrogen atom or acetylamino group, and $R^4$ is 2-pyrrolidinoethyl, 2-piperidinoethyl or 2-morpholinoethyl group.

The compound (I) in which $R^4$ is a group of the formula:

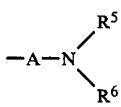

and A is a lower alkylene group containing hydroxy group or a branched-lower alkylene group (e.g., methylethylene) can exist in the form of two optical isomers. The present invention also includes these optical isomers or a mixture thereof within its scope.

According to the present invention, the compound (I) in which Y is oxygen atom or imino group, i.e., the compound of the formula:

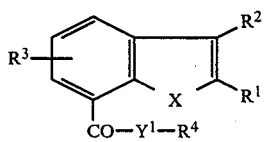

wherein $Y^1$ is oxygen atom or imino group, and $R^1$, $R^2$, $R^3$, $R^4$ and X are the same as defined above, or a salt thereof can be prepared by the step or steps of:

[A-(1)] condensing the following two compounds of the formula:

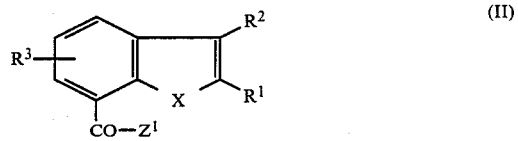

and

wheren one of $Z^1$ and $Z^2$ is a group of the formula: —$Y^1$—H and the other is a reactive residue, or $Z^1$ is hydroxy group and $Z^2$ is a group of the formula: —$Y^1$—H, and $R^1$, $R^2$, $R^3$, $R^4$, X and $Y^1$ are the same as defined above; and

[A-(2)] if required, further converting the thus-obtained product into a salt thereof.

Alternatively, the compound (I) in which Y is oxygen atom, i.e., the compound of the formula:

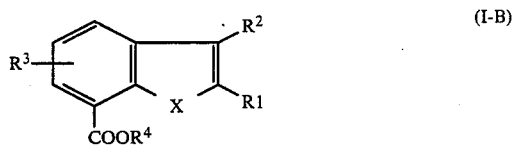

wherein $R^1$, $R^2$, $R^3$, $R^4$ and X are the same as defined above, or a salt can be prepared by the step or steps of:

[B-(1)] subjecting a compound of the formula:

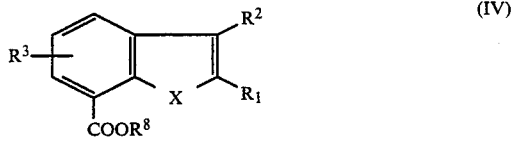

wherein $R^8$ is a lower alkyl group, and $R^1$, $R^2$, $R^3$ and X are the same as defined above and a compound of the formula:

wherein $R^4$ is the same as defined above to transesterification reaction; and

[B-(2)] if required, further converting the thus-obtained product into a salt thereof.

Further, the compound (I) in which Y is a lower alkylimino group or a phenyl-lower alkylimino group, i.e., the compound of the formula:

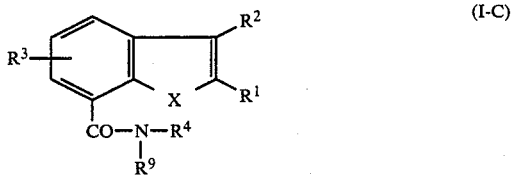

wherein $R^9$ is a lower alkyl group or a phenyl-lower alkyl group, $R^1$, $R^2$, $R^3$, $R^4$ and X are the same as defined above, or a salt thereof can be prepared by the step or steps of:

[C-(1)] reacting a compound of the formula:

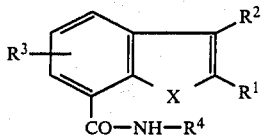

(I-D)

wherein $R^1$, $R^2$, $R^3$, $R^4$, and X are the same as defined above, with a compound of the formula:

$$R^9-W \qquad (V)$$

wherein $R^9$ is the same as defined above and W is a reactive residue; and

[C-(2)] if required, further converting the product into a salt thereof.

[D] When $R^1$ is a phenyl group substituted with nitro group and/or $R^3$ is nitro group, said nitro group(s) may be if required, reduced to amino group(s) and said amino groups(s) may be, if required, further acylated to acylamino group(s), before the step A-(2), B-(2) or C-(2).

In the above-mentioned reactions, the starting compounds (II), (III), (IV) and (I-D), if required, can be used in the form of a salt thereof. Examples of the salt of said compounds include hydrochloride, hydrobromide, sulfate, oxalate, fumarate, methansulfonate and the like. Further, when one of $Z^1$ and $Z^2$ is a reactive residue, examples of the reactive residue include a halogen atom such as chlorine, bromine or iodine. Moreover, examples of the reactive residue W include a halogen atom such as chlorine or bromine, methanesulfonyloxy and p-toluenesulfonyloxy.

[Step A-(1)]

The condensation reaction of the compound (II) ($Z^1$=reactive residue) with the compound (III) ($Z^2$=—$Y^1$—H) and the condensation reaction of the compound (II) ($Z^1$=—$Y^1$—H) with the compound (III) ($Z^1$=reactive residue) can be carried out in the presence or absence of an acid acceptor in a solvent. Suitable examples of the solvent which is used in the former condensation reaction are dichloromethane, dichloroethane, chloroform, carbon tetrachloride, ether, tetrahydrofuran, pyridine, benzene, toluene and the like. On the other hand, suitable examples of the solvent which is used in the latter condensation reaction are lower alkanoyl (e.g., methanol, ethanol and the like), acetone, tetrahydrofuran, dioxane, dimethylsulfoxide, dimethylformamide and the like. Examples of the acid acceptor include, for example, inorganic bases such as alkali metal hydroxides (e.g., sodium hydroxide, potassium hydroxide), alkali metal carbonates (e.g., sodium carbonate, potassium carbonate), alkali metal bicarbonate (e.g., sodium bicarbonate, potassium bicarbonate), alkaline earth metal hydroxides (e.g., calcium hydroxide, barium hydroxide) or silver hydroxide; and organic bases such as triethylamine or pyridine. It is preferred to carry out the reaction at a temperature of 0° to 100° C., especially 0° to 30° C.

Concomitantly, the starting compound (II) in which $Z^1$ is a reactive residue can be prepared by reacting the compound (II) in which $Z^1$ is hydroxy group, with a halogenating agent (e.g., a thionyl halide such as thionyl chloride or thionyl bromide, an oxalyl halide such as oxalyl chloride or oxalyl bromide).

Further, the condensation reaction of the compound (II) ($Z^1$=hydroxy group) with the compound (III) ($Z^2$=—$Y^1$—H) can be carried out in the presence of a condensing agent in a solvent. Chloroform, dichloromethane, tetrahydrofuran, dimethylsulfoxide, acetonitrile and the like are suitable as the solvent. Suitable examples of the condensing agent include N,N-dicyclohexylcarbodiimide, a combination of N,N-dicyclohexylcarbodiimide and N-hydroxysuccinimide or N-hydroxybenzotriazole, carbonyldiimidazole, ethyl chlorocarbonate, isobutyl chlorocarbonate and the like. It is prefered to carry out the reaction at a temperature of −20° to 50° C., especially 0° to 30° C.

[Step B-(1)]

The transesterification reaction between the compound (IV) and the compound (III-A) can be carried out in the presence of a catalyst in a solvent. Examples of the catalyst include orthotitanic acid esters such as tetraethyl orthotitanate, tetrapropyl orthotitanate, tetraisopropyl orthotitanate or tetrabenzyl orthotitanate and alkali metals such as sodium. Dimethyfomamide, dimethylsulfoxide, benzene, xylene and the like are preferably used as the solvent. It is preferred to carry out the reaction at a temperature of 20° to 150° C., especially 80° to 150° C.

[Step C-(1)]

The reaction of the compound (I-D) with the compound (V) can be carried out in the presence of an acid acceptor in a solvent. Dimethylformamide, tetrahydrofuran, dimethylsulfoxide, dioxane and the like are preferablly used as the solvent. Examples of the acid acceptor include alkali metal hydroxides such as sodium hydroxide or potassium hydroxide, alkali metal hydrides such as sodium hydride, alkali metal carbonates such as sodium carbonate or potassium carbonate, alkali metal alkoxides such as sodium methoxide or sodium ethoxide and the like. It is preferred to carry out the reaction at a temperature of −10° to 100° C., especially at −10° to 20° C. in case the alkali metal hydride is used, or at 50° to 100° C. in case the alkali metal hydroxide or alkali metal carbonate is used.

[Step D]

The optional reduction of the nitro group(s) can be conducted in a traditional manner. For example, said reduction can be carried out by treating the nitro-compound obtained in Step A-(1), Step B-(1) or Step C-(1) either with a reducing agent (e.g., stannous chloride, tin-acetic acid, tin-mineral acid, iron-acetic acid, iron-mineral acid and the like) or with ammonium formate or hydrogen gas in the presence of a catalyst (e.g., palladium-carbon, platinum, Raney nickel and the like). It is preferred to carry out the reaction in a solvent (e.g., methanol, ethanol, tetrahydrofuran, ethyl acetate and the kike) at a temperature of 20° to 100° C., especially at 50° to 100° C. in case the reducing agent is used, at 50° to 80° C. in case ammonium formate is used, or at room temperature in case hydrogen gas is used.

The optional acylation of the amino-compound obtained in the afore-mentioned reduction can be carried out by treating said compound with an acylating agent in the presence or absence of an acid acceptor in a solvent. Examples of the acylating agent include reactive derivatives (e.g., anhydride or halide such as chloride) of lower alkanoic acids (e.g., acetic acid) or phenyl-lower alkanoic acids (e.g., phenylacetic acid). Ethyl acetate, benzene, toluene or a mixture of water and said organic solvent is preferably used as the solvent. Examples of the acid acceptor include alkali metal carbonates such as sodium carbonate or potassium carbonate, alkali metal bicarbonates such as sodium bicarbonate or potassium bicarbonate, alkali metal hydrides such as sodium hydride, alkali metal alkoxides such as sodium methoxide or sodium ethoxide, tri-lower alkylamine such as triethylamine and pyridine. It is preferred to carry out the reaction at a temperature of 0° to 100° C., especially 0° to 50° C.

[Steps A-(2), B-(2) and C-(2)]

The compound (I) obtained in the above-mentioned reactions can be readily converted into a salt thereof in a traditional manner, for example, by treatment with an acid.

As mentioned hereinbefore, the benzo-furan(or -thiophene) derivative (I) of the present invention and a salt thereof have a potent inhibitory activity against the reflective contraction of urinary bladder and are useful for treatment and/or prophylaxis of urinary system diseases associated with contracting function disorder of urinary bladder or ureter, for example, pollakiuria (frequent micturition), dyuria (painful urination), nocturia (voiding during the night), enuresis (bed-wetting at night), irritable bladder, and the like.

The compound (I) of the present invention can be used for pharmaceutical use either in the free form or in the form of a pharmaceutically acceptable salt thereof. Examples of the salt of the compound (I) include inorganic acid addition salts such as hydrochloride, hydrobromide or sulfate, and organic acid addition salts such as oxalate, sulfamate, acetate, fumarate, maleate, citrate or methanesulfonate.

The compound (I) or a salt thereof can be administered either orally or parenterally. For oral administration, the compound (I) and a salt thereof may be used in the solid form such as tablets, powders, capsules or granules, which may contain conventional carriers, binders, diluents, disintegrators, wetting agents and the like. They may also be used in liquid form such as aqueous or oily suspensions, solutions, syrups or elixirs. On the other hand, for parenteral administration, the compound (I) and a salt thereof may be used, for example, in the form of injections.

The dose of the compound (I) or a salt thereof may vary over a wide range depending on the administration route, the age, body weight or conditions of patients and the kind and severity of diseases to be treated. In general, however, preferred daily dose of the compound (I) or a salt thereof is in the range of 0.2 to 30 mg/kg/day, especially 3 to 30 mg/kg/day in case of oral administration, or 0.2 to 2 mg/kg/day in case of parenteral administration.

Concomitantly, the starting compound (II) in which $Z^1$ is hydroxy group or a group of the formula: —$Y^1$—H and the compound (IV) may be prepared by either one of the methods shown in the following reaction schemes (a) to (f). Besides, the starting compound (IV) may also be prepared by esterifying the compound (II) in which $Z^1$ is hydroxy group. Further, the starting compound (II) in which $Z^1$ is hydroxy group may also be prepared by hydrolyzing the compound (IV) obtained in the methods shown in the following reaction schemes. Furthermore, the starting compounds (II) and (IV) in which $R^1$ is an acylaminophenyl group or a di(lower alkyl)aminophenyl group may also be prepared by reducing the corresponding nitropheny-compounds, followed by acylation or alkylation. Moroever, the compound (II) and (IV) in which $R^3$ is hydrogen atom, may be prepared by reducing the compound (II) in which $R^3$ is a halogen atom, and the compound (II) and (IV) in which $R^3$ is an acylamino group may be prepared by reducing the compounds (II) and (IV) in which $R^3$ is nitro group, followed by acylation.

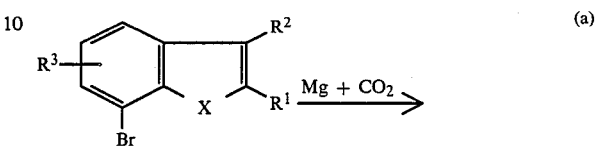

(a)

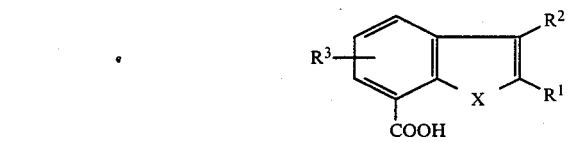

(b)

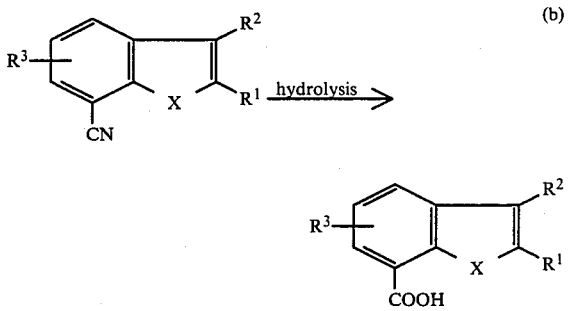

(c)

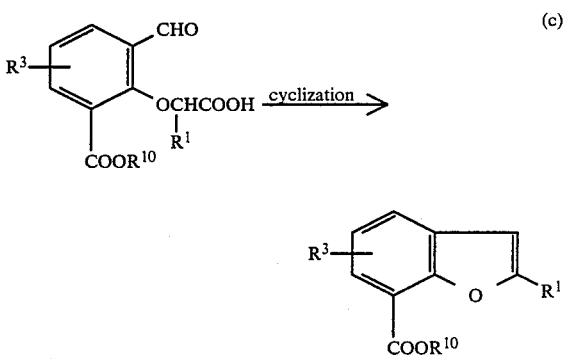

(d)

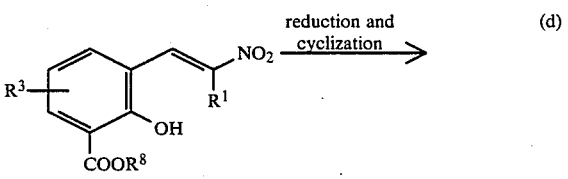

(e)

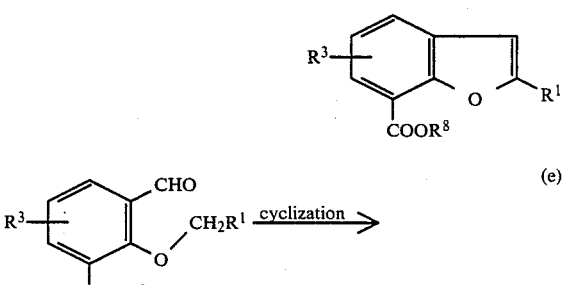

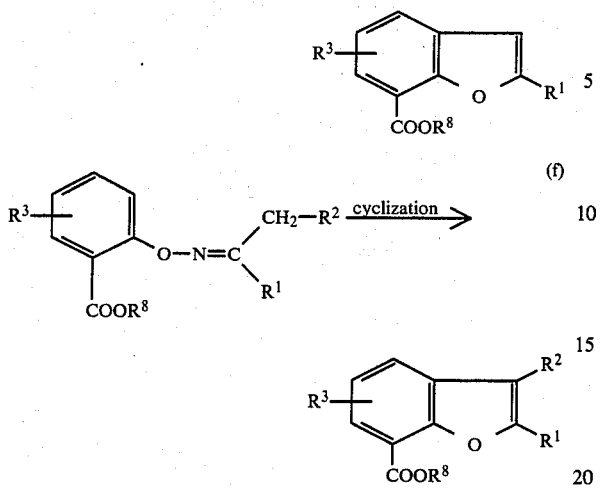

(f)

In the above-mentioned reactions (a) to (f), $R^{10}$ is hydrogen atom or a lower alkyl group, and $R^1$, $R^2$, $R^3$, $R^8$ and X are the same as defined above.

On the other hand, the starting compound (II) in which $Z^1$ is amino group (i.e., the compound (II) in which $Z^1$ is a group of the formula: $-Y^1-H$ and $Y^1$ is imino group) may be prepared by amidating the compound (IV) in a traditional manner.

Throughout the specification and claims, the terms "lower alkyl", "lower alkoxy", "lower alkanoyl" and "lower alkylene" should be interpreted as referring to straight or branched alkyl of one to 6 carbon atoms, straight or branched alkoxy of one to 6 carbon atoms, straight or branched alkanoyl of 2 to 7 carbon atoms and straight or branched alkylene of one to 6 carbon atoms, respectively.

Experiment (Method)

Female rats (body weight: 200–300 g; age: 10–14 weeks old) were anesthetized with urethane (1.0–1.2 g/kg, s.c.). A catheter was inserted into the urinary bladder via the urethra meatus of each of the rats and the external urethral orifice was ligated. One end of the catheter was connected to a syringe filled with saline and a pressure transducer through a T-tube. Saline was injected into the urinary bladder via the catheter, and the change in intravesical pressure was measured. A physiological saline solution was injected into the urinary bladder. After it was confirmed that rhythmical contractions occured, a test compound (dose: 2–4 mg/kg) dissolved in a physiological saline solution was administered to the rat through a catheter inserted into the femoral vein. The rhythmical contraction loss time (i.e., a period of time from disappearance of contractions to recovery thereof) was measured and the inhibitory activity of the test compound against rhythmical contractions of urinary bladder was estimated by comparing said rhythmical contraction loss time with that in the case of administration of flavoxate hydrochloride (dose: the same as the test compound).

(Result)

The following compounds shown in Table 1 exhibited more than 1.5 times stronger inhibitory activity against contractions of the urinary bladder than flavoxate hydrochloride.

TABLE 1

| Comp. No. | X | $R^1$ | $R^2$ | $R^3$ | $R^4$ | salt |
|---|---|---|---|---|---|---|
| 1 | O | | H | H | $-(CH_2)_2N$⟨pyrrolidinyl⟩ | hydrochloride |
| 2 | O | | H | H | $-(CH_2)_2N$⟨morpholinyl⟩ | hydrochloride |
| 3 | O | | H | H | $-(CH_2)_2N$⟨piperidinyl⟩ | hydrochloride |
| 4 | O | | H | H | $-CH_2-$(N-methylpiperidinyl) | hydrochloride |

TABLE 1-continued

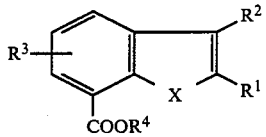

| Comp. No. | X | R¹ | R² | R³ | R⁴ | salt |
|---|---|---|---|---|---|---|
| 5 | O | H | H | H | —(CH₂)₂N⟨⟩ | hydrochloride |
| 6 | O | CH₃ | H | H | —(CH₂)₂N⟨⟩ | hydrochloride |
| 7 | O | —⟨⟩—NO₂ | H | H | —(CH₂)₂N⟨⟩ | methanesulfonate |
| 8 | O | —⟨⟩ | H | —NHCOCH₃ | —(CH₂)₂N⟨⟩ | hydrochloride |
| 9 | S | H | —⟨⟩ | H | —(CH₂)₂N⟨⟩ | hydrochloride |

EXAMPLE 1

(1) A mixture of 102 g of 5-chloro-2-hydroxybenzoic acid, 166 g of hexamethylenetetramine and 600 ml of trifluoroacetic acid is heated at 100° C. overnight. 2.95 liters of water and 1.48 liters of 10% hydrochloric acid are added to the mixture and said mixture is heated at the same temperature for 15 minutes. After cooling, the resultant crystals are collected by filtration to give 96.9 g of 5-chloro-3-formyl-2-hydroxybenzoic acid.

M.p. 218° C.

(2) 193 g of 5-chloro-3-formyl-2-hydroxybenzoic acid are dissoved in 2 liters of methanol and the solution is saturated with hydrogen chloride. 100 ml of thionyl chloride are added to the solution and the mixture is refluxed for 8 hours. After cooling, the resultant crystals are collected by filtration and dried to give 190 g of methyl 5-chloro-3-formyl-2-hydroxybenzoate.

m.p. 132°–134° C.

(3) A mixture of 3.0 g of methyl 5-chloro-3-formyl-2-hydroxybenzoate, 3.44 g of methyl α-bromophenylacetate, 8.28 g of potassium carbonate and 50 ml of dimethylformamide is heated at 70°–80° C. for 15 minutes and further heated at 100° C. for 10 minutes. After cooling, water is added to the mixture, and the aqueous mixture is acidified with 10% hydrochloric acid and then extracted with ethyl acetate. The extract is washed with an aqueous saturated sodium chloride solution, dried and evaporated to remove solvent. The residue is dissolved in 50 ml of ethanol, and 4.5 g of potassium hydroxide are added to the solution. The mixture is refluxed for 1 hour and then evaporated to remove solvent. Water is added to the residue, and the aqueous mixture is acidified with 10% hydrochloric acid and extracted with ethyl acetate. The extract is dried and evaporated to remove solvent. 150 ml of xylene and 30 mg of p-toluenesulfonic acid are added to the residue and the mixture is refluxed for 1 hour. The reaction mixture is evaporated to remove solvent and the residue is dissolved in ethyl acetate. The solution is washed, dried and evaporated to remove solvent. The residue is crystallized from isopropyl ether to give 2.32 g of 5-chloro-2-phenylbenzofuran-7-carboxylic acid.

M.p. 255°–258° C.

(4) 1.46 g of 5-chloro-2-phenylbenzofuran-7-carboxylic acid are dissolved in a mixture of 15 ml of ethyleneglycol monomethylethers and 15 ml of methanol. 500 mg of 10% palladium-carbon and 1.6 g of ammonium formate are added to the solution and the solution is heated at 40° C. for 1.5 hours. The reaction mixture is filtered and the filtrate is concentrated under reduced pressure. The residue is dissolved in ethyl acetate. The solution is washed successively with 10% hydrochloric acid and water, dried and evaporated to remove solvent to give 2-phenylbenzofuran-7-carboxylic acid.

M.p. 212°–214° C.

(5) 1.10 g of 2-phenylbenzofuran-7-carboxylic acid are dissolved in a mixture of 25 ml of tetrahydrofuran and 25 ml of benzene, and 1.27 g of oxalyl chloride and 2 drops of dimethylformamide are added to the solution. The mixture is stirred at room temperature for 1 hour. The reaction mixture is evaporated to remove solvent and the residue is dissolved in 20 ml of methylene chloride. The solution is added dropwise to a mixture of 0.98 g of 2-(dimethylamino)ethanol and 0.91 g of triethylamine in 20 ml of methylene chloride under ice-cooling. The mixture is stirred at the same temperature for 30 minutes. The reaction mixture is washed with water, dried and evaporated to remove solvent. The residue is recrystallized from n-hexane to give 1.29 g of 2-(dimethylamino)ethyl 2-phenylbenzofuran-7-carboxylate.

M.p. 56.5°–58° C.

Hydrochloride: colorless needles.

M.p. 183°–185° C. (recrystallized from methanol-ether).

EXAMPLE 2

A mixture of 1.5 g of 2-phenylbenzofuran-7-carboxylic acid, 4.5 ml of thionyl chloride, 0.2 ml of pyridine and 20 ml of chloroform is stirred at room temperature for 2 hours and evaporated under reduced pressure to remove solvent. The residue is dissolved in 20 ml of methylene chloride and the solution is added dropwise to a solution of 0.8 g of 2-pyrrolidinoethanol and 1.27 g of triethylamine in 20 ml of methylene chloride under ice-cooling. The mixture is stirred at the same temperature for 1 hour. The reaction mixture is washed with water, dried and evaporated to remove solvent. The residue is treated with hydrochloric acid-ether and recrystallized from isopropanolisopropyl ether to give 1.96 g of 2-pyrrolidinoethyl 2-phenylbenzofuran-7-carboxylic hydrochloride as colorless needles.

M.p. 165°–167° C.

EXAMPLE 3–18

The corresponding starting compounds are treated in the same manner as described in Example 1-(5) or Example 2 to give the following compounds shown in Table 2.

TABLE 2

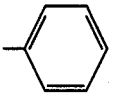

(I-a)

| Exp. Nos. | Compound (I-a) | | | properties |
|---|---|---|---|---|
| | R¹ | R³ | R⁴ | |
| 3 | 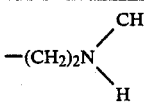 | H | —(CH₂)₂N(CH₃)H | hydrochloride yield: 73.8% M.p. 178–182° C. (recrystallized from isopropanol) |
| 4 | 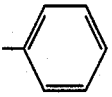 | H | —(CH₂)₂N(CH₃)(CH₂-phenyl) | oxalate yield: 70.9% M.p. 149–150° C. (recrystallized from isopropanol) |
| 5 | 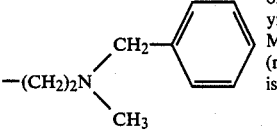 | H | —(CH₂)₂N(morpholino) | hydrochloride yield: 75.1% M.p. 185–187° C. (recrystallized from isopropanol-isopropyl ether) |
| 6 | 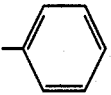 | H | —(CH₂)₃N(pyrrolidino) | hydrochloride yield: 85.2% M.p. 188–189° C. (recrystallized from isopropanol) |
| 7 | 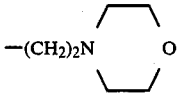 | H | —(CH₂)₂N(piperidino) | hydrochloride yield: 81.5% M.p. 178–180° C. (recrystallized from ethanol-ether) |
| 8 | 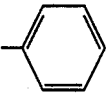 | H | —(CH₂)₃N(piperidino) | hydrochloride yield: 80.8% M.p. 194–195° C. (recrystallized from isopropanol) |
| 9 | 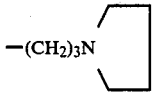 | H | —(CH₂)₄N(piperidino) | hydrochloride yield: 82.0% M.p. 183–185° C. (recrystallized from isopropanol) |

TABLE 2-continued

| Exp. Nos. | Compound (I-a) R¹ | R³ | R⁴ | properties |
|---|---|---|---|---|
| 10 |  | H | —(CH₂)₅N | sulfate<br>yield: 75.0%<br>M.p. 146–149° C.<br>(recrystallized from ethanol-ether) |
| 11 | 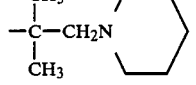 | H | $\begin{array}{c}CH_3\\|\\-C-CH_2N\\|\\CH_3\end{array}$ | oxalate<br>yield: 57.0%<br>M.p. 155.5–156.5° C.<br>(recrystallized from tetrahydrofuran) |
| 12 | 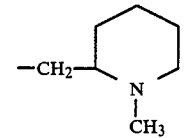 | H | —CH₂— | hydrochloride<br>yield: 78.5%<br>M.p. 218–219° C.<br>(recrystallized from isopropanol) |
| 13 | 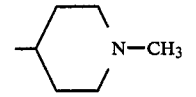 | H |  | hydrochloride<br>yield: 63.6%<br>M.p. 243–245° C.<br>(recrystallized from isopropanol) |
| 14 | 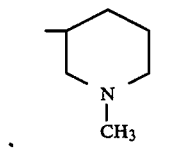 | H | 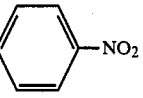 | hydrochloride<br>yield: 50.9%<br>M.p. > 167° C. (decomp.)<br>(recrystallized from isopropanol-acetonitrile) |
| 15 | 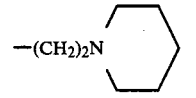 | H | —(CH₂)₂N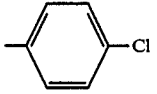 | methanesulfonate<br>yield: 74.7%<br>M.p. 186–187° C.<br>(recrystallized from ethanol-ether) |
| 16 | 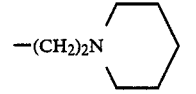 | H | —(CH₂)₂N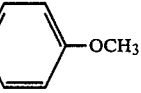 | hydrochloride<br>yield: 68.4%<br>M.p. 215–216° C.<br>(recrystallized from isopropanol) |
| 17 | 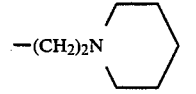 | H | —(CH₂)₂N | hydrochloride<br>yield: 72.0%<br>M.p. 199–205° C.<br>(recrystallized from isopropanol) |
| 18 | 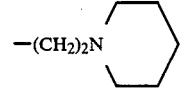 | Cl | —(CH₂)₂N | hydrochloride<br>yield: 89.5%<br>M.p. 227–229° C.<br>(recrystallized from methanol-ether) |

EXAMPLE 19

(1) 2.5 g of 2-phenylbenzofuran-7-carboxylic acid is dissolved in a mixture of 80 ml of methanol and 16 ml of tetrahydrofuran and 0.5 g of platinum oxide is added to the solution. The mixture is subjected to catalytic hydrogenation under atmospheric pressure. The reaction mixture is filtered and the filtrate is evaporated to remove solvent. The residue is purified by silica gel column chromatography (solvent; chloroform:methanol=20:1) to give 1.54 g of 2-cyclohexylbenzofuran-7-carboxylic acid as colorless oil.

Mass(m/e): 244 (M+).

(2) 1.22 g of 2-cyclohexylbenzofuran-7-carboxylic acid is treated in the same manner as described in Example 1-(5) to give 1.12 g of 2-piperidinoethyl 2-cyclohexylbenzofuran-7-carboxylate oxalate. yield: 50.2%.

M.p. >165° C. (recrystallized from isopropanol-ether).

EXAMPLE 20

(1) 15 g of 2-hydroxy-5-methoxybenzoic acid is treated in the same manner as described in Example 1-(1) to (3) to give 10.8 g of 5-methoxy-2-phenylbenzofuran-7-carboxylic acid. yield: 45%.
M.p. 185°–187° C.

(2) 1.34 g of 5-methoxy-2-phenylbenzofuran-7-carboxylic acid and 0.77 g of 2-piperidinoethanol are treated in the same manner as described in Example 1-(5) to give 2.08 g of 2-piperidinoethyl 5-methoxy-2-phenylbenzofuran-7-carboxylate hydrochloride.
yield: 77.5%.
M.p. 200°–202° C. (recrystallized from isopropanol).

EXAMPLE 21–24

(1)-(i) A mixture of 420 mg of methyl benzofuran-7-carboxylate, 5 ml of an aqueous 10% sodium hydroxide solution and 5 ml of methanol is stirred at room temperature for 1 hour. The reaction mixture is evaporated to remove solvent. The residue is dissolved in water and the solution is acidified with 10% hydrochloric acid. The resultant crystals are collected by filtration and dried to give 321 mg of benzofuran-7-carboxylic acid as colorless crystals.
M.p. 159°–161° C.

The corresponding methyl ester compounds are treated in the same manner as described above to give the following compounds.

(ii) 2-methylbenzofuran-7-carboxylic acid
M.p. 144°–147° C. (recrystallized from aqueous ethanol).

(iii) 2-benzylbenzofuran-7-carboxylic acid white powder
IR $\nu_{max}^{Nujol}$ (cm$^{-1}$): 1680.

(iv) 5-nitro-2-phenylbenzofuran-7-carboxylic acid
M.p. 297°–298.5° C. (decomp.) (recrystallized from tetrahydrofuran-n-hexane).

(2) The compounds obtained in (1)-(i), (ii), (iii) or (iv) and 2-piperidinoethanol are treated in the same manner as described in Example 2 to give the following compounds shown in Table 3.

TABLE 3

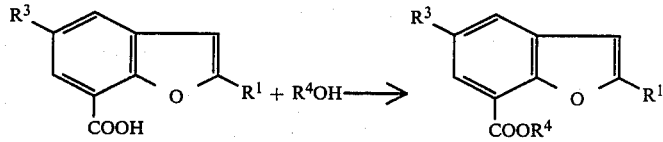

(I-a)

| Ex. Nos. | Compound (I-a) | | | |
|---|---|---|---|---|
| | R$^1$ | R$^3$ | R$^4$ | Properties |
| 21 | H | H | —(CH$_2$)$_2$N⟨piperidino⟩ | hydrochloride yield: 71.5% M.p. 210–212° C. (recrystallized from isopropanol) |
| 22 | CH$_3$ | H | —(CH$_2$)$_2$N⟨piperidino⟩ | hydrochloride yield: 71.2% M.p. 200–202° C. (recrystallized from isopropanol-isopropyl ether) |
| 23 | —CH$_2$—C$_6$H$_5$ | H | —(CH$_2$)$_2$N⟨piperidino⟩ | hydrochloride yield: 68.8% (recrystallized from isopropanol-isopropyl ether) |
| 24 | —C$_6$H$_5$ | NO$_2$ | —(CH$_2$)$_2$N⟨piperidino⟩ | methanesulfonate yield: 91.1% M.p. 201.5–202.5° C. (recrystallized from tetrahydrofuran-ether) |

EXAMPLE 25

(1) A diazomethane-ether solution (prepared from 5.0 g of nitrosomethylurea) is added to a solution of 6.0 g of 2-(4-nitrophenyl)benzofuran-7-carboxylic acid in 60 ml of tetrahydrofuran and the mixture is stirred at room temperature for 1 hour. The reaction mixture is evaporated to remove solvent and the residue is dissolved in ethyl acetate. The solution is washed with water, dried and evaporated to remove solvent. The residue is washed with ethyl acetate and dried to give 3.82 g of methyl 2-(4-nitrophenyl)benzofuran-7-carboxylate as pale brown powder.
IR $\nu_{max}^{Nujol}$ (cm$^{-1}$): 1720.

(2) A mixture of 3.1 g of methyl 2-(4-nitrophenyl)benzofuran-7-carboxylate, 11.7 g of stannous chloride dihydrate and 100 ml of ethyl acetate is heated at 70° C. for 1 hour. After cooling, the reaction mixture is alkalized with an aqueous sodium bicarbonate solution and extracted with ethyl acetate. The extract is washed with water, dried and evaporated to remove solvent to give 2.6 g of methyl 2-(4-aminophenyl)benzofuran-7-carboxylate as yellow crystals.
M.p. 158°–161° C.

(3) A mixture of 2.6 g of methyl 2-(4-aminophenyl)-benzofuran-7-carboxylate, 1.52 ml of methyl iodide, 6.72 g of potassium carbonate and 25 ml of dimethylformamide is stirred at room temperature for 1 hour. 2.2 ml of methyl iodide are added to the mixture and the mixture is stirred for 2 hours. The reaction mixture is poured into water and the aqueous mixture is extracted with ethyl acetate. The extract is washed with water, dried and evaporated to remove solvent. The residue is purified by silica gel column chromatography (solvent; n-hexane:ethyl acetate=1:4) to give 2.0 g of methyl 2-(4-dimethylaminophenyl)benzofuran-7-carboxylate as orange needles.

M.p. 145°–148° C.

(4) 920 mg of methyl 2-(4-dimethylaminophenyl)benzofuran-7-carboxylate are dissolved in a mixture of 20 ml of methanol and 20 ml of tetrahydrofuran. 10 ml of an aqueous 1N sodium hydroxide solution are added to the solution and the mixture is heated at 50° C. for 40 minutes. After cooling, the reaction mixture is neutralized with 10% hydrocloric acid and extracted with ethyl acetate. The extract is dried and evaporated to remove solvent to give 870 mg of 2-(4-dimethylaminophenyl)benzofuran-7-carboxylic acid as yellow powder.

IR $\nu_{max}^{Nujoul}$ (cm$^{-1}$): 1690.

(5) 0.61 g of 2-(4-dimethylaminophenyl)benzofuran-7-carboxylic acid and 0.56 g of 2-piperidinoethanol are treated in the same manner as described in Example 1-(5) to give 0.82 g of 2-piperidinoethyl 2-(4-dimethylaminophenyl)benzofuran-7-carboxylate oxalate as yellow powder. Yield: 78.8%

IR $\nu_{max}^{Nujol}$ (cm$^{-1}$): 1710.

EXAMPLE 26

(1) A solution of 5.0 g of propiophenone oxime in 35 ml of dimethylformamide is added dropwise to a solution of 1.55 g of 62.5% sodium hydride in 80 ml of dimethylformamide under ice-colling, and the mixture is stirred at the same temperature for 20 minutes. A solution of 4.24 g of 2-chlorobenzonitrile in 20 ml of dimethylformamide is added dropwise to the mixture and the mixture is stirred at room temperature for 3 hours. The reaction mixture is poured into ice-water and the aqueous mixture is extracted with ethyl acetate. The extract is washed with a saturated sodium chloride solution, dried and evaporated to remove solvent. The residue is purified by silica gel column chromatography (solvent; n-hexane:ethyl acetate=6:1) to give 2.19 g of propiophenone O-(2-cyanophenyl)oxime as oil.

IR $\nu_{max}^{Nujol}$ (cm$^{-1}$): 2225.

(2) A mixture of 227 mg of propiophenone O-(2-cyanophenyl)oxime and 5 ml of 21% hydrochloric acid-ethanol is refluxed for 1 hour and the reaction mixture is evaporated to remove solvent. The residue is dissolved in ethyl acetate, and the solution is washed with water, dried and evaporated to remove solvent. The residue is purified by silica gel column chromatography (solvent; n-hexane:ethyl acetate=6:1) and recrystallized from isopropanol to give 63 mg of 3-methyl-2-phenylbenzofuran-7-nitrile as colorless needles.

M.p. 86°–87° C.

(3) A mixture of 364 mg of 3-methyl-2-phenylbenzofuran-7-nitrile, 3 g of an aqueous 30% sodium hydroxide solution and 8 ml of ethylene glycol is refluxed for 2 hours. After cooling, the reaction mixture is poured into water, acidified with 10% hydrochloric acid and then extracted with ethyl acetate. The extract is washed with a saturated sodium chloride solution, dried and evaporated to remove solvent. The residue is recrystallized from tetrahydrofuran-n-hexane to give 257 mg of 3-methyl-2-phenylbenzofuran-7-carboxylic acid as colorless prisms.

M.p. 219.5°–222.5° C.

(4) 0.37 g of 3-methyl-2-phenylbenzofuran-7-carboxylic acid and 0.23 g of 2-piperidinoethanol are treated in the same manner as described in Example 2 to give 0.43 g of 2-piperidinoethyl 3-methyl-2-phenylbenzofuran-7-carboxylate hydrochloride as colorless needles. yield: 73.6%.

M.p. 190°–191.5° C. (recrystallized from isopropanol).

EXAMPLE 27

A mixture of 1.16 g of 2-phenylbenzofuran-7-carboxylic acid, 1.0 g of 2-(diisopropylamino)ethyl chloride hydrochloride, 0.66 g of potassium hydroxide and 20 ml of isopropanol is refluxed for 1 hour. After cooling, ethyl acetate and water are added to the reaction mixture. The organic layer is collected, washed with a saturated sodium chloride solution and evaporated to remove solvent. The residue is purified by silica gel column chromatography (solvent; chloroform:methanol=20:1) to give 1.51 g 2-(diisopropylamino)ethyl 2-phenylbenzofuran-7-carboxylate as colorless oil.

Hydrochloride: colorless needles

M.p. 199.5°–201.5° C. (recrystallized from methanol-ether).

EXAMPLE 28

1.43 g of 2-phenylbenzofuran-7-carboxylic acid are dissolved in 10 ml of tetrahydrofuran, and 1.08 g of carbonyldiimidazole are added to the solution. The mixture is stirred at room temperature for 2 hours and a solution of 0.76 g of 2-(t-butylamino)ethanol in 4 ml of tetrahydrofuran is added thereto. The mixture is stirred at room temperature for 15 hours and evaporated to remove solvent. Water is added to the residue and the aqueous mixture is extracted with ethyl acetate. The extract is washed with water, dried, and evaporated to remove solvent to give 1.72 g of 2-(t-butylamino)ethyl 2-phenylbenzofuran-7-carboxylate as pale yellow oil.

Methanesulfonate: colorless needles

M.p. 249°–250° C. (recrystallized from methanol-ether).

EXAMPLE 29–31

The corresponding starting compounds are treated in the same manner as described in Example 28 to give the following compounds shown in Table 4.

TABLE 4

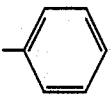

(I-B)

| Ex. Nos. | Compound (I-b) R¹ | A | Properties |
|---|---|---|---|
| 29 | 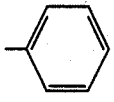 | —CH(CH₃)—CH₂— | oxalate yield: 70.0% M.p. 148.5–149.5° C. (recrystallized from isopropanol) |
| 30 | 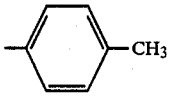 | —CH₂—CH(OH)—CH₂— | hydrochloride yield: 67.0% M.p. 192–197° C. (recrystallized from isopropanol) |
| 31 | (4-CH₃-C₆H₄—) | —(CH₂)₂— | hydrochloride yield: 73.0% M.p. 201–202° C. (recrystallized from isopropanol-ether) |

EXAMPLE 32–33

(1)-(i) A suspension of 6.72 g of 60% sodium hydride in 40 ml of tetrahydrofuran is added dropwise to a solution of 24.17 g of 2-bromophenol in 210 ml of tetrahydrofuran at 4° C. and the mixture is stirred at the same temperature for 15 minutes. A solution of 30.66 g of phenacyl bromide in 60 ml of tetrahydrofuran is added dropwise to the mixture. The mixture is stirred at the same temperature for 30 minutes and further refluxed for 2.5 hours. The reaction mixture is evaporated to remove solvent, and water is added to the residue. The aqueous mixture is extracted with ethyl acetate and the extract is washed, dried and evaporated to remove solvent. The residue is purified by silica gel column chromatography and recrystallized from a mixture of ethyl acetate and n-hexane to give 21.49 g of (2-bromophenyl)(benzoylmethyl)ether as colorless needles.

M.p. 111.5°–113° C.

(2)-(i) 21.49 g of (2-bromophenyl)(benzoylmethyl)ether are added to 180 ml of polyphosphoric acid and the mixture is stirred at 123° C. for 2.5 hours. After cooling, the reaction mixture is poured into ice-water and extracted with ethyl acetate. The extract is washed successively with water and an aqueous sodium bicarbonate solution, dried and evaporated to remove solvent. The residue is purified by silica gel column chromatography and recrystallized from aqueous ethanol to give 10.04 g of 7-bromo-3-phenylbenzofuran as colorless needles.

M.p. 69.5°–71.5° C.

(3)-(i) 2.4 ml of methyl iodide are added dropwise to a solution of 3.9 g of magnesium in 16 ml of tetrahydrofuran and the mixture is stirred at room temperature for 20 minutes. A solution of 11.0 g of 7-bromo-3-phenylbenzofuran in tetrahydrofuran is added dropwise to the mixture and the mixture is refluxed for 4 hours. After cooling, the reaction mixture is poured to dry ice, acidified with 10% hydrochloric acid and extracted with ethyl acetate. The extract is washed with water, dried and evaporated to remove solvent. The residue is recrystallized from ethyl acetate to give 6.31 g of 3-phenylbenzofuran-7-carboxylic acid as pale yellow prisms.

M.p. 220°–222° C.

2-Bromothiophenol instead of 2-bromophenol is treated in the same manner as described in Step (1)-(i)-(3)-(i) to give the following compound.

(ii) 3-phenylbenzothiophene-7-caboxylic acid: pale yellow needles

M.p. 277°–282° C. (decomp.) (recrystallized from ethanol).

(4) The compound obtained in Step (3)-(i) or (ii) and 2-piperidinoethanol are treated in the same manner as described in Example 28 to give the following compounds.

(32) 2-piperidinoethyl 3-phenylbenzofuran-7-carboxylate; yield: 60% colorless needles

M.p. 201°–202° C. (recrystallized from isopropanol).

(33) 2-piperidinoethyl 3-phenylbenzothiophene-7-carboxylate; yield: 72% colorless needles

M.p.>205° C. (decomp.) (recrystallized from isopropanol).

EXAMPLE 34

(1) 7.0 g of 2-phenylbenzofuran-7-carboxylic acid are dissolved in 70 ml of methanol, and 6.4 ml of thionyl chloride are added dropwise thereto at 0° C. The mixture is refluxed for 1 hour and evaporated to remove solvent. The residue is dissolved in ethyl acetate, and the solution is washed with water, dried and evaporated to remove solvent. The residue is recrystallized from n-hexane to give 7.04 g of methyl 2-phenylbenzofuran-7-carboxylate as colorless needles.

M.p. 45°–47° C.

(2) A mixture of 0.76 g of methyl 2-phenylbenzofuran-7-carboxylate, 0.46 g of 2-piperidinoethanol, 0.05 g of tetraisopropyl orthotitanate and 5 ml of xylene is refluxed for 4 hours. Toluene and an aqueous 10% sodium hydroxide solution are added to the reaction mixture and the mixture is filtered. The filtrate is washed with water, dried and evaporated to remove solvent. The residue is purified by silica gel column chromatography (solvent; chloroform:methanol=10:1) to give 1.01 g of 2-piperidinoethyl 2-phenylbenzofuran-7-carboxylate as pale yellow oil.

IR$\nu_{max}^{Nujol}$ (cm$^{-1}$): 1710.

EXAMPLE 35–37

The corresponding starting compounds are treated in the same manner as described in Example 34-(2) to give the following compounds shown in Table 5.

TABLE 5

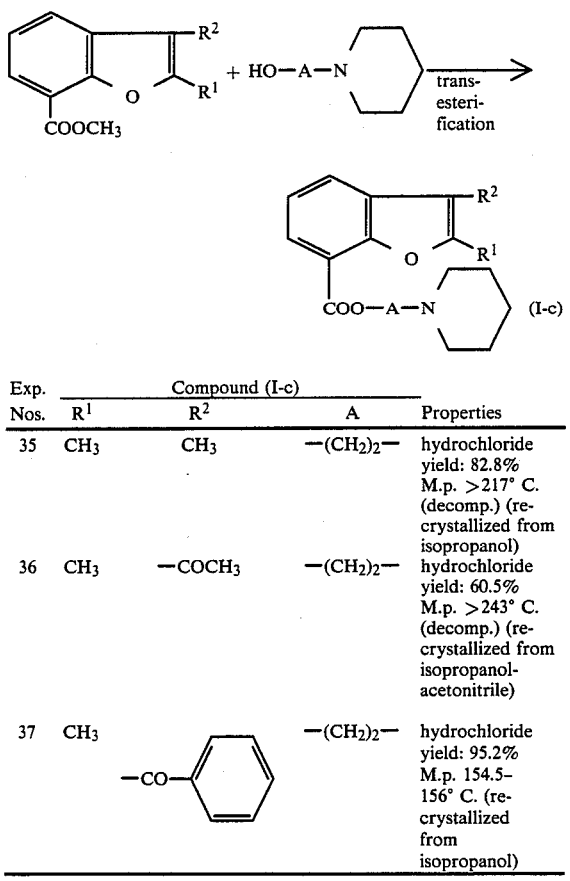

| Exp. Nos. | R¹ | R² | A | Properties |
|---|---|---|---|---|
| 35 | CH₃ | CH₃ | —(CH₂)₂— | hydrochloride yield: 82.8% M.p. >217° C. (decomp.) (recrystallized from isopropanol) |
| 36 | CH₃ | —COCH₃ | —(CH₂)₂— | hydrochloride yield: 60.5% M.p. >243° C. (decomp.) (recrystallized from isopropanol-acetonitrile) |
| 37 | CH₃ | —CO—C₆H₅ | —(CH₂)₂— | hydrochloride yield: 95.2% M.p. 154.5–156° C. (recrystallized from isopropanol) |

EXAMPLE 38

A mixture of 1.5 g of 2-piperidinoethyl 5-nitro-2-phenylbenzofuran-7-carboxylate, 4.29 g of stannous chloride dihydrate and 100 ml of ethyl acetate is heated at 70°–80° C. for 2 hours. The reaction mixture is neutralized with an aqueous saturated sodium bicarbonate solution and extracted with ethyl acetate. The extract is washed, dried and evaporated to remove solvent. The residue is recrystallized from isopropanol to give 995 mg of 2-piperidinoethyl 5-amino-2-phenylbenzofuran-7-carboxylate as yellow needles.

M.p. 126.5°–128° C.

Dioxalate: pale yellow needles

M.p.>105° C. (decomp.) (recrystallized from tetrahydrofuran).

EXAMPLE 39

1.18 g of 2-piperidinoethyl 2-(4-nitrophenyl)benzofuran-7-carboxylate is treated in the same manner as described in Example 38 to give 0.76 g of 2-piperidinoethyl 2-(4-aminophenyl)benzofuran-7-carboxylate as colorless needles. yield: 70%.

IR$\nu_{max}^{Nujol}$(cm$^{-1}$): 3480, 3380, 1710.

hydrochloride: pale yellow powder

M.p.>170° C. (decomp.) (recrystallized from methanol-ether).

EXAMPLE 40

A solution of 147 mg of acetyl chloride in 2 ml of toluene is added dropwise to a mixture of 522 mg of 2-piperidinoethyl 5-amino-2-phenylbenzofuran-7-carboxylate, 210 mg of sodium bicarbonate and 10 ml of ethyl acetate under ice-cooling. The mixture is stirred at the same temperature for 30 minutes and the reaction mixture is extracted with ethyl acetate. The extract is washed with water, dried and evaporated to remove solvent. The residue is recrystallized from ethyl acetate to give 467 mg of 2-piperidinoethyl 5-acetamido-2-phenylbenzofuran-7-carboxylate as pale yellow needles.

M.p. 172.5°–174° C.

hydrochloride: colorless needles

M.p. 255°–257° C. (decomp.) (recrystallized from isopropanol).

EXAMPLE 41

0.65 g of 2-piperidinoethyl 2-(4-aminophenyl)benzofuran-7-carboxyate is treated in the same manner as described in the same manner as described in Example 40 to give 0.53 g of 2-piperidinoethyl 2-(4-acetamidophenyl)benzofuran-7-carboxylate as yellow needles. yield: 73.6%.

M.p. 155°–157° C.

EXAMPLE 42

3.0 g of 2-phenylbenzofuran-7-carboxylic acid are dissolved in 40 ml of chloroform, and 9 ml of thionyl chloride and 0.4 ml of pyridine are added thereto. The mixture is stirred at room temperature for 2 hours. The reaction mixture is evaporated to remove solvent and the residue is dissolved in 40 ml of methylene chloride. The solution is added dropwise to a solution of 1.78 g of N-(2-aminoethyl)piperidine and 2.55 g of triethylamine in 30 ml of methylene chloride under ice-cooling and the mixture is stirred at the same temperature for 1 hour. The reaction mixture is washed with water, dried and evaporated to remove solvent. The residue is crystallized from ether to give 4.12 g of 2-phenylbenzofuran-7-N-(2-piperidinoethyl)carboxamide as colorless needles.

M.p. 75°–77° C. (recrystallized from ethanol-ether).

Oxalate: colorless needles

M.p. 187°–188° C. (recrystallized from ethanol-ether).

EXAMPLE 43

490 mg of 2-phenylbenzofuran-7-carboxylic acid are dissolved in 10 ml of chloroform, and 0.5 ml of oxalyl chlorode and 0.1 ml of pyridine are added thereto. The mixture is stirred at room temperature for 3 hours. The reaction mixture is evaporated under reduced pressure to remove solvent and the residue is dissolved in 5 ml of methylene chloride. The solution is added dropwise to a solution of 340 mg of N,N-diethylethylenediamine and 290 mg of triethylamine in 10 ml of methylene chloride under ice-cooling. The mixture is stirred at the same temperature for 1 hour. The reaction mixture is washed with water, dried and evaporated to remove solvent. The residue is crystallized from ether to give 660 mg of 2-phenylbenzofuran-7-N-[2-(diethylamino)ethyl]carboxamide as yellow oil.

IR$\nu_{max}^{liquid}$(Cm$^{-1}$): 3410, 1660.

Oxalate: colorless needles

M.p. 165°–167° C. (recrystallized from ethanol-ether).

EXAMPLE 44

1.68 g of 2-phenylbenzofuran-7-N-[2-(diethylamino)ethyl]carboxamide are dissolved in 5 ml of dimethylformamide and the solution is added dropwise to a suspension of 0.24 g of 62.5% sodium hydride in 10 ml of dimethylformamide under ice-cooling. The mixture is stirred at room temperature for 30 minutes and 0.83 g of methyl iodide is added to the mixture. The mixture is stirred for 3 hours. The reaction mixture is poured into ice-water and the aqueous mixture is extracted with ethyl acetate. The extract is washed with water, dried and evaporated to remove solvent. The residue is treated with hydrochloric acid-ether and recrystallized from ethanol-ether to give 1.44 g of 2-phenylbenzofuran-7-N-[2-(diethylamino)ethyl]-N-methylcarboxamide hydrochloride as pale yellow needles.

M.p. 191°–193° C.

EXAMPLE 45

1.3 g of 2-phenylbenzofuran-7-N-[2-(diethylamino)ethyl]carboxamide and 0.63 g of benzyl chloride are treated in the same manner as described in Example 44 to give 1.44 g of 2-phenylbenzofuran-7-N-benzyl-N-[2-(diethylamino)ethyl]carboxamide hydrochloride.

M.p. 209°–211° C. (recrystallized from ethanol).

Preparation 1

(1) A mixture of 73.2 g of 5-chloro-3-formyl-2-hydroxybenzoic acid, 350 ml of ethylene glycol and 129 ml of trimethylchlorosilane is stirred at room temperature for 2 hours. The reaction mixture is poured into a mixture of an aqueous saturated sodium bicarbonate solution and trimethylamine, and the mixture is extracted with ethyl acetate. The extract is washed with water, dried and evaporated to remove solvent to give 86 g of methyl 5-chloro-3-(1,3-dioxolan-2-yl)-2-hydroxybenzoate as yellow powder.

(2) 86 g of methyl 5-chloro-3-(1,3-dioxolan-2-yl)-2-hydroxybenzoate are dissolved in a mixture of 700 ml of methanol and 50 ml of tetrahydrofuran, and 70 ml of triethylamine and 7 g of 10% palladium-carbon are added to the solution. The mixture is subjected to catalytic hydrogenation under atmospheric pressure. The reaction mixture is filtered and the filtrate is evaporated to remove solvent. 10% hydrochloric acid is added to the residue and the mixture is concentrated. Water is added to the residue and the aqueous mixture is extracted with ethyl acetate. The extract is dried and evaporated to remove solvent. The resultant crystals are collected, washed with cold ethanol and dried to give 51.1 g of methyl 3-formyl-2-hydroxybenzoate as colorless needles.

M.p. 82°–84° C.

(3) A mixture of 2.0 g of methyl 3-formyl-2-hydroxybenzoate, 3.51 g of methyl α-bromo-p-chlorophenylacetate, 5.55 g of potassium carbonate and 60 ml of dimethylformamide is heated at 70°–80° C. for 15 minutes and further heated at 100° C. for 10 minutes. The reaction mixture is filtered and washed with ethyl acetate. The washings and the filtrate are combined and water is added to the mixture. The mixture is acidified with 10% hydrochloric acid. The organic layer is collected and the aqueous layer is extracted with ethyl acetate. The organic layer and the extract are combined, washed with water, dried and evaporated to remove solvent. The residue is dissolved in 30 ml of ethanol and 3.25 g of potassium hydroxide are added to the solution. The mixture is refluxed for 1 hour. The reaction mixture is evaporated to remove solvent, and water is added to the residue. The aqueous mixture is acidified with 10% hydrochloric acid and extracted with ethyl acetate. The extract is washed with water, dried and evaporated to remove solvent. 100 ml of xylene and 150 mg of p-toluenesulfonic acid are added to the residue and the mixture is refluxed for 1 hour. After cooling, ethyl acetate is added to the reaction mixture. The mixture is washed with water, dried and evaporated to remove solvent. The residue is recrystallized from ethyl acetate to give 1.84 g of 2-(4-chlorophenyl)benzofuran-7-carboxylic acid as colorless needles.

M.p. 228°–230° C.

The corresponding starting compounds are treated in the same manner as described above to give the following compounds.

(i) 2-(4-methylphenyl)benzofuran-7-carboxylic acid

M.p. 227°–229° C. (recrystallized from ethyl acetate-n-hexane)

(ii) 2-(4-methoxyphenyl)benzofuran-7-carboxylic acid

M.p. 249°–250.5° C. (recrystallized from tetrahydrofuran-isopropyl ether).

Preparation 2

(1) A mixture of 5.0 g of methyl 3-formyl-2-hydroxybenzoate, 11.7 g of 4-nitrobenzyl bromide, 11.7 g of potassium carbonate and 70 ml of dimethylformamide is stirred at room temperature for 1 hour. The reaction mixture is poured into water and the aqueous mixture is extracted with ethyl acetate. The extract is dried and evaporated to remove solvent to give 8.70 g of methyl 3-formyl-2-(4-nitrobenzyloxy)benzoate as colorless powder.

(2) 16.1 g of methyl 3-formyl-2-(4-nitrobenzyloxy)benzoate are dissolved in 100 ml of dimethylformamide and a solution of 5.4 g of sodium methoxide in 20 ml of methanol is added dropwise to the solution at 120° C. The mixture is stirred at the same temperature for 10 minutes. The reaction mixture is acidified with 10% hydrochloric acid and then extracted with ethyl acetate. The extract is washed with water, dried and evaporated to remove solvent. The resultant crystals are collected, washed and dried to give 8.65 g of 2-(4-nitrophenyl)benzofuran-7-carboxylic acid as pale orange powder.

IR$\nu_{max}^{Nujol}$(cm$^{-1}$): 1710.

Preparation 3

(1) A mixture of 1.90 g of methyl 3-formyl-2-hydroxybenzoate, 3.0 g of nitroethane, 0.15 ml of piperidine and 30 ml of toluene is refluxed overnight while removing water. The reaction mixture is poured into ice-water and the aqueous mixture is extracted with ethyl acetate. The extract is washed successively with 10% hydrochloric acid and an aqueous saturated sodium chloride solution, dried and evaporated to remove solvent. The residue is recrystallized from methanol to give 2.05 g of methyl 2-hydroxy-3-(2-nitro-1-propenyl)benzoate.

M.p. 119°–121° C.

(2) A mixture of 2.02 g of methyl 2-hydroxy-3-(2-nitro-1-propenyl)benzoate, 4.75 g of iron powder and 40 ml of acetic acid is heated at 70° C. for 25 minutes. Toluene is added to the reaction mixture, and the mixture is filtered and washed with chloroform. The washings and the filtrate are combined and the mixture is evaporated under reduced pressure to remove solvent. 50 ml of toluene, 2.43 g of p-toluenesulfonic acid monohydrate and 1 ml of water are added to the residue. The mixture is refluxed for 50 minutes and further refluxed 20 minutes while removing water azeotropically. Ethyl acetate is added to the reaction mixture. The mixture is washed successively with water and an aqueous saturated sodium bicarbonate solution, dried and evaporated to remove solvent. The residue is purified by silica gel column chromatography to give 1.24 g of methyl 2-methylbenzofuran-7-carboxylate as colorless oil.

Mass(m/e): 190 (M+).

The corresponding starting compound is treated in the same manner as described above to give the following compound.

(i) methyl 2-benzylbenzofuran-7-carboxylate
IR$\nu_{max}^{liquid}$(cm$^{-1}$): 1720.

Preparation 4

(1) A mixture of 3.0 g of methyl 3-formyl-2-hydroxybenzoate, 3.31 g of t-butyl chloroacetate, 12.0 g of potassium carbonate and 40 ml of dimethylformamide is heated at 70° C. for 2.5 hours. After cooling, the reaction mixture is poured into water and the aqueous mixture is extracted with ethyl acetate. The extract is washed with an aqueous saturated sodium chloride solution, dried and evaporated to remove solvent. The residue is dissolved in trifluoroacetic acid and the solution is stirred at room temperature for 30 minutes. The reaction mixture is concentrated under reduced pressure and the residue is treated with ether to give 2.09 g of (2-methoxycarbonyl-6-formylphenoxy)acetic acid as pale yellow powder.

(2) A mixture of 2.09 g of (2-methoxycarbonyl-6-formylphenoxy)acetic acid, 1.48 g of sodium acetate and 7 ml of acetic anhydride is refluxed for 1.5 hours. After cooling, water is added to the reaction mixture, and the aqueous mixture is alkalized with potassium carbonate and extracted with ethyl acetate. The extract is washed with water, dried and evaporated to remove solvent. The residue is purified by silica gel column chromatography to give 0.39 g of methyl benzofuran-7-carboxylate as colorless oil.

IR$\nu_{max}^{liquid}$(cm$^{-1}$): 1720.

Preparation 5

(1) A solution of 17.25 g of acetophenone oxime in 100 ml of dimethylformamide is added dropwise to a suspension of 5.92 g of 62.5% sodium hydride in 400 ml of dimethylformamide under ice-cooling. The mixture is stirred at the same temperature for 1.5 hours. A solution of 25.04 g of methyl 2-chloro-5-nitrobenzoate in 150 ml of dimethylformamide is added to the mixture, the mixture is stirred for 1 hour. The reaction mixture is poured into ice-water and the aqueous mixture is extracted with ethyl acetate. The extract is washed with an aqueous saturated sodium chloride solution, dried and evaporated to remove solvent. The residue is recrystallized from isopropanol to give 26.7 g of acetophenone O-(2-methoxycarbonyl-4-nitrophenyl)oxime as yellow needles.

M.p. 108.5°–109.5° C.

(2) A mixture of 26.7 g of acetophenone O-(2-methoxycarbonyl-4-nitrophenyl)oxime and 250 ml of formic acid is refluxed for 6 hours and the reaction mixture is evaporated under reduced pressure to remove solvent. The residue is recrystallized from ethyl acetate to give 9.22 g of methyl 5-nitro-2-phenylbenzofuran-7-carboxylate as yellow needles.

M.p. 186°–188.5° C.

Preparation 6

(1) 5.3 g of methyl 3-acetylsalicylate are dissolved in 50 ml of dimethylformamide and the solution is added dropwise to a suspension of 1.26 g of 62.5% sodium hydride in 15 ml of dimethylformamide, and the mixture is stirred for 20 minutes. 5.40 g of methyl 2-bromo-propionate are added dropwise to the mixture and the mixture is heated at 60°–80° C. for 7 hours. The reaction mixture is poured into ice-water and the aqueous mixture is extracted with ethyl acetate. The extract is washed with water, dried and evaporated to remove solvent. The residue is purified by silica gel column chromatography (solvent; n-hexane:ethyl acetate=3:1) to give 5.10 g of methyl 2-(2-methoxycarbonyl-6-acetylphenoxy)propionate as colorless oil.

(2) A mixture of 4.42 g of methyl 2-(2-methoxycarbonyl-6-acetylphenoxy)propionate, 20 ml of 6N hydrochloric acid and 20 ml of dioxane is refluxed for 10 minutes, and water is added to the reaction mixture. The aqueous mixture is extracted with ethyl acetate. The extract is washed with water, dried and evaporated to remove solvent. The residue is dissolved in 30 ml of tetrahydrofuran, and 5.55 ml of oxalyl chloride and a drop of dimethylformamide are added to the solution. The mixture is stirred for 1 hour. The reaction mixture is evaporated to remove solvent and the residue is dissolved in 100 ml of benzene. The solution is added dropwise to a refluxed solution of 6.66 ml of triethylamine in benzene and the mixture is refluxed for 5 hours. The reaction mixture is washed successively with 2% hydrochloric acid and water, dried and evaporated to remove solvent. The residue is purified by silica gel column chromatography (solvent; n-hexane:ethyl acetate=5:1) to give 1.48 g of methyl 2,3-dimethylbenzofuran-7-carboxylate.

M.p. 54.5°–55.5° C.

Preparation 7

A mixture of 1.0 g of methyl 2-methylbenzofuran-7-carboxylate, 1.24 g of acetyl chloride, 2.15 g of aluminum chloride and 20 ml of dichloroethane is heated at 50°–60° C. for 1 hour. The reaction mixture is poured into ice-water and the aqueous mixture is extracted with chloroform. The extract is washed with water, dried and evaporated to remove solvent. The residue is recrystallized from ethyl acetate-n-hexane to give 1.08 g of methyl 3-acetyl-2-methylbenzofuran-7-carboxylate as colorless needles.

M.p. 115°–117° C.

(i) The corresponding starting compounds are treated in the same manner as described above to give methyl 3-benzoyl-2-methylbenzofuran-7-carboxylate as colorless needles.

M.p. 70°–72° C. (recrystallized from isopropyl ether).

What we claim is:

1. A benzofuran compound of the formula:

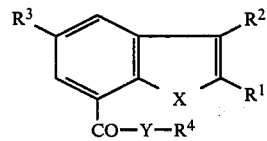

wherein $R^1$ is hydrogen atom, a lower alkyl group, phenyl group or nitrophenyl group, $R^2$ is a hydrogen atom, $R^3$ is a hydrogen atom, nitro group, a lower alkoxy group, or a lower alkanoyl amino group, $R^4$ is a group of the formula:

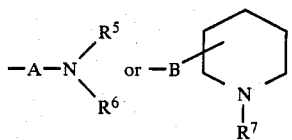

wherein A is a lower alkylene group, B is a lower alkylene group, $R^5$ and $R^6$ combine to form a pyrrolidino, piperidino or morpholino group, $R^7$ is a lower alkyl group, X is an oxygen atom, and Y is an oxygen atom, or a salt thereof.

2. The compound according to claim 1, in which $R^1$ is a hydrogen atom, a $C_{1-4}$ alkyl group, phenyl group or nitrophenyl group, $R^3$ is a hydrogen atom, nitro group, a $C_{1-4}$ alkoxy group or a $C_{2-5}$ alkanoylamino group, A is a $C_{1-6}$ alkylene group, B is a $C_{1-6}$ alkylene group and $R^7$ is a $C_{1-4}$ alkyl group.

3. The compound according to claim 1, in which A is a $C_{1-4}$ alkylene group and B is a $C_{1-4}$ alkylene group.

4. The compound according to claim 1, in which $R^1$ is a hydrogen atom, methyl group, phenyl group or nitrophenyl group, $R^3$ is a hydrogen atom or acetylamino group, and $R^4$ is 2-pyrrolidinoethyl, 2-piperidinoethyl or 2-morpholinoethyl group.

5. The compound according to claim 4, which is 2-pyrrolidinoethyl 2-phenylbenzofuran-7-carboxylate or a salt thereof.

6. The compound according to claim 4, which is 2-piperidinoethyl 2-phenylbenzofuran-7-carboxylate or a salt thereof.

7. The compound according to claim 4, which is 2-morpholinoethyl 2-phenylbenzofuran-7-carboxylate or a salt thereof.

8. A pharmaceutical composition exhibiting inhibitory activity against reflective contraction of urinary bladder which comprises a therapeutically effective amount of the compound claimed in claim 1 and a pharmaceutically acceptable carrier therefor.

9. A method for treatment or prophylaxis of pollakiuria, dyuria, nocturia, enuresis or irritable bladder in a warm-blooded animal, which comprises administering to said warm-blooded animal a therapeutically effective amount of the compound claimed in claim 1.

* * * * *